United States Patent [19]
Ellison

[11] 4,129,127
[45] Dec. 12, 1978

[54] METHOD OF MAKING A SURGICAL CAST

[76] Inventor: Francis D. Ellison, 5005 E. 10th St., Indianapolis, Ind. 46201

[21] Appl. No.: 780,709

[22] Filed: Mar. 24, 1977

[51] Int. Cl.² .............................................. A61F 5/04
[52] U.S. Cl. ................................ 128/89 R; 128/91 R
[58] Field of Search ...................... 128/89 R, 90, 91 R

[56] References Cited

U.S. PATENT DOCUMENTS

| | | | |
|---|---|---|---|
| 323,775 | 8/1885 | Bender et al. ...................... | 128/89 R |
| 2,761,443 | 9/1956 | Parker ................................ | 128/91 R |
| 3,631,855 | 1/1972 | Fehlau .................................... | 128/90 |
| 3,955,565 | 5/1976 | Johnson, Jr. ........................ | 128/89 R |

FOREIGN PATENT DOCUMENTS 1233172  5/1971  United Kingdom ...................... 128/90

*Primary Examiner*—John D. Yasko
*Attorney, Agent, or Firm*—Woodard, Weikart, Emhardt & Naughton

[57] ABSTRACT

A body portion to be immobilized is wrapped with appropriate padding. Two flexible barrier members are secured to the padding on diametrically opposite sides of the body portion. Successive layers of gauze impregnated with plaster are applied to a sector of the body portion between the barriers, wetted and allowed to set. Detents in the barrier members are effective to form mating detents in the edges of the rigid shell thus formed. The barriers are then removed while the shell remains in place. The barrier edges of the shell are coated with a release agent. Layers of impregnated gauze are applied to the opposite sector of the body portion between the edges of the first shell, wetted and allowed to set. The detents in the edges of the first shell thereby form corresponding mating detents in the edges of the second shell thus formed. After setting, the shells are secured together by wrapping with an ace bandage webbing or the like.

7 Claims, 12 Drawing Figures

METHOD OF MAKING A SURGICAL CAST

BACKGROUND OF THE INVENTION

1. Field of the Invention

This invention relates generally to preparation of surgical casts, and more particularly to the preparation of a surgical cast which can be readily removed and re-installed on the patient.

2. Description of the Prior Art

For many years, surgical casts have had the common disadvantages of bulk, weight, and hand tailoring in each case. The hand tailoring would not be a particular nuisance if it were necessary only once during the entire period of time that a patient might need to wear a cast. However, it is known that there are instances when it is necessary to remove a cast entirely, or at least cut away a portion of a cast, and then prepare a new cast in the one instance, and fill in the removed portion in the other instance. Each time such procedure requires the time and skill necessary to remove or cut away a portion of the cast, plus the time and skill necessary to make a new cast, or make a filler for the portion which has been cut away.

The removal or opening of portions of casts is necessary for various reasons, including inspection of the wound, application of new dressing, growth of the patient, relief of pressure from swelling, or for other reasons. Such eventualities result in the aforementioned requirements of time and effort in the removal and replacement processes.

The aforementioned problems have been recognized and workers in the arts have developed various types of casts and methods in efforts to overcome such problems. Those known to me as a result of a search of prior art patents are represented by the following U.S. Pat. Nos. 2,103,942, Gillin, Dec. 28, 1937; 2,480,849, Gersh et al., Sept. 6, 1949; 2,761,443, Parker, Sept. 4, 1956; 3,032,033, Ramirez, May 1, 1962; 3,085,569, Cook et al., Apr. 16, 1963; 3,389,700, Whyte, June 25, 1968.

Although the foregoing patents represent good efforts, there have remained certain problems. There has remained a need for a cast which can be prepared conveniently and simply using the techniques and procedures which are generally familiar to orthopedic surgeons, as well as familiar materials, and which will combine the features of lightness, durability and minimal bulk.

SUMMARY OF THE INVENTION

Described briefly, in a typical embodiment of the present invention, a cast for immobilizing a portion of an animal body is made of two shells. These shells are made sequentially. The first shell is made by laying up on the body portion to be encased, a cast-forming material in an unrigid condition and molding it to a pair of barriers which have been previously secured, though temporarily, to the body portion. Once in place, the material is rigidized, as by setting of plaster of Paris, for example. Then the barriers are removed. Then a release agent is applied to the edges which were formed against the barriers. Next the second shell is laid up, using the same kind of molding material which is subsequently rigidized or set, to complete the encasement. Then the two shells are permanently secured in place by some attachment means such as wrapping them with an ace bandage, or the use of Velcro fasteners, or some garter or other type of securing means to prevent the two shells from separating. Detent means in the mating edges of the shells prevent them from moving relative to each other in any direction except that in which they can be separated when it is desired to separate the shells for inspection of the body portion.

The garter means do accommodate swelling as caused by inflammation or growth, without impeding circulation in the body member.

DESCRIPTION OF THE PREFERRED EMBODIMENT

Figure 1:
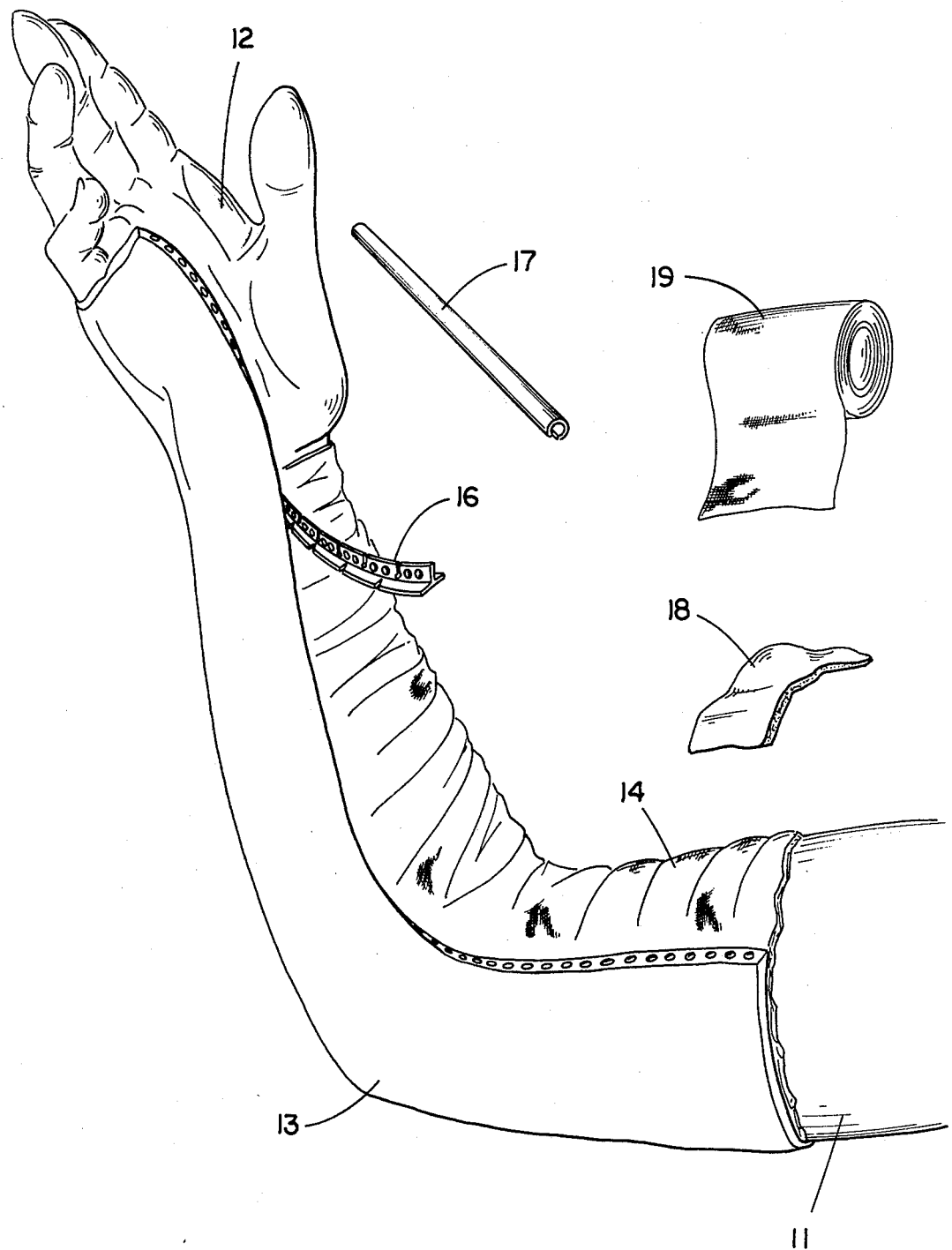
FIG. 1 is an illustrative view of an arm and wrist cast partially completed according to a typical embodiment of the present invention.

Referring now to the drawings in detail, and particularly FIG. 1, the arm 11 and hand 12 are provided with a cast of which the first half is shown at 13. This has been applied over a cotton wrapping 14. A barrier strip 16, enforcement tube 17, unset cast material 18, and ace bandage roll 19 are also shown. The specific nature and use of these items will now be described.

Figure 2:
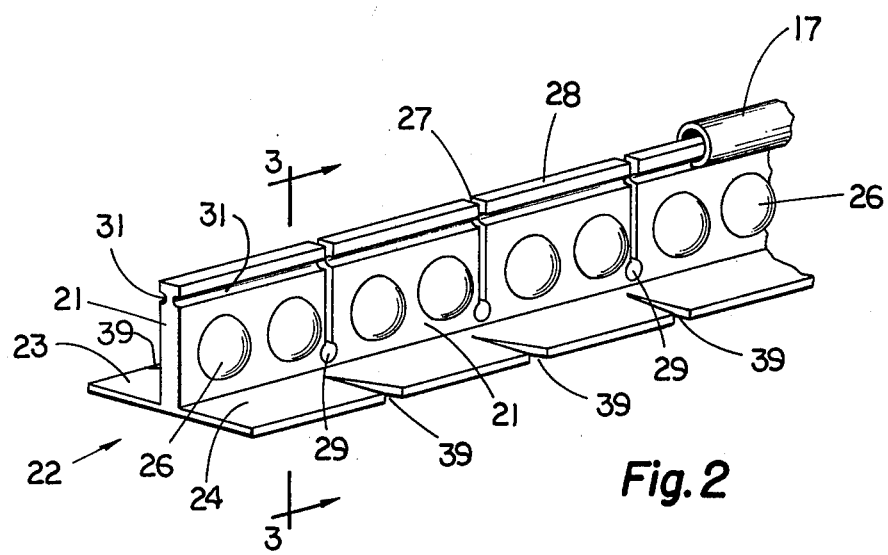
FIG. 2 is an enlarged perspective view of a barrier strip employed therein.
Figure 3:
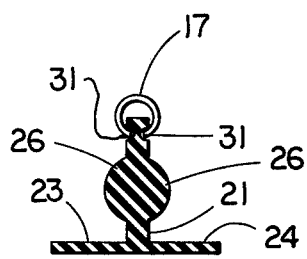
FIG. 3 is a cross section through the barrier strip taken at line 3—3 in FIG. 2 and viewed in the direction of the arrows.
Figure 4:
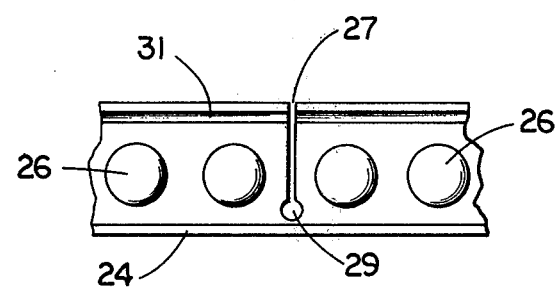
FIG. 4 is a side elevational view of a fragment thereof.

Referring now to FIG. 2, there is shown one form of the barrier strip useful according to a typical embodiment of this invention. This strip may be made of molded rubber and in a continuous roll, if desired. The surgeon preparing the cast can cut from the roll a length suitable in accordance with the length of the cast to be made. The barrier is of a generally T-shaped configuration including the central wall 21 and base 22, the latter comprising a pair of horizontally-extending flanges 23 and 24. The wall has a plurality of longitudinally-spaced detent means in the form of spherical bulges 26 on both faces as better shown in FIG. 3. It also has a plurality of longitudinally-spaced slots 27 opening at the upper edge of the wall or rib 28. The lower end of these slots at 29 may be enlarged, if desired, or it may be the same width as the overall height of the slot, although the enlarged configuration is preferable. This is immediately above the upper face of the flanges 23 and 24. Also there is a split tube 17 mounted on the rib and the lower edges of the split in the tube being received in the grooves 31 in the opposite faces of the rib 21.

Figure 5:
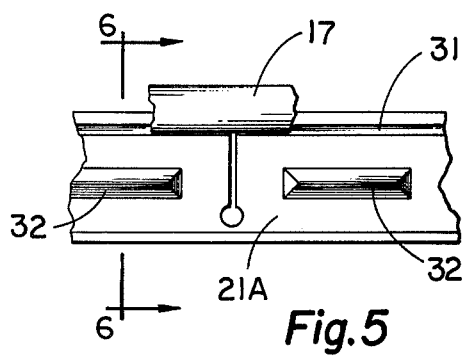
FIG. 5 is a side elevational view of a fragment of an alternative embodiment of the barrier strip of FIGS. 2, 3 and 4.
Figure 6:
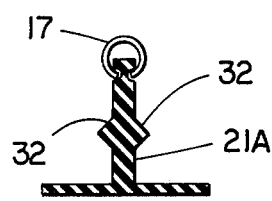
FIG. 6 is a cross section taken at lines 6—6 in FIG. 5 and viewed in the direction of the arrows.

A similar construction is shown for an alternate embodiment of the barrier member in which generally elongated angular detent bosses or protrusions 32 are provided in the vertical rib 21A of the barrier shown in FIGS. 5 and 6.

METHOD

Figure 7:
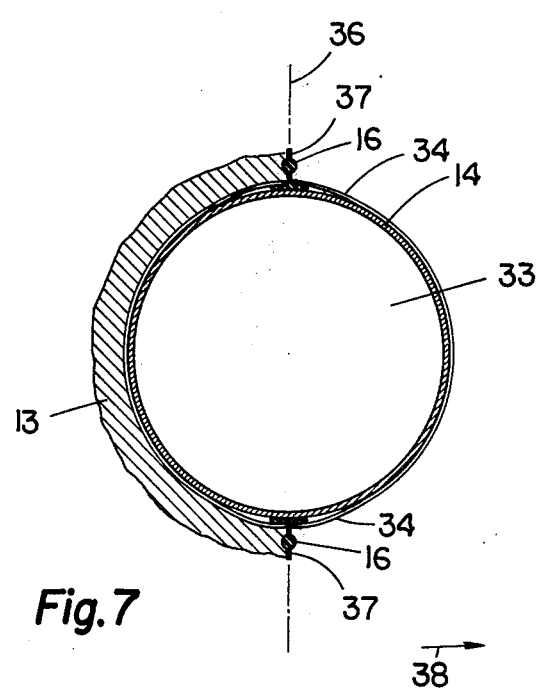
FIG. 7 is a cross sectional view through an arm on which the cast is being applied according to a typical embodiment of the present invention.
Figure 8:
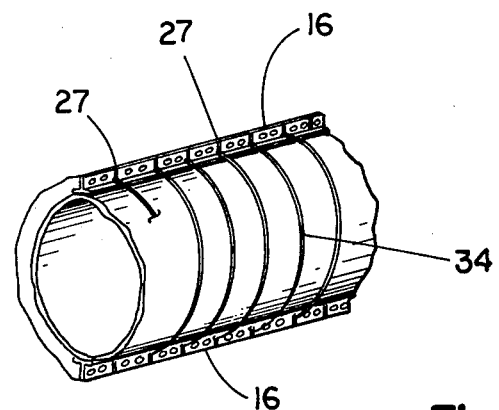
FIG. 8 is a fragmentary perspective view of the arm and cast portion at the stage represented by FIG. 7.
Figure 9:
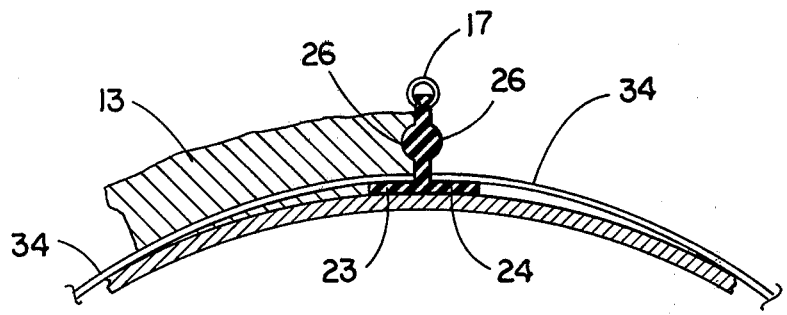
FIG. 9 is an enlarged fragmentary portion of the view of FIG. 7.

According to the preferred method of the invention, the body portion to be immobilized is first wrapped with suitable dressing or padding. Referring to FIG. 7, for example, where a body limb such as an arm is generally indicated at 33, it may be first wrapped with cotton 14 or other suitable dressing and protective padding material. Then two barrier strips 16 are mounted at diametrically opposite locations on the limb and extend throughout the length which the cast is to have. These are mounted by simply placing them with the base flanges thereof flat against the padding 14. Then an elastic binding is wrapped around the limb to secure the barrier strips to it. Typically a continuous rubber band 34 can be employed for this purpose, and it is spiral-wound around the limb such as shown in FIG. 8 where the band 34 is received in each of the slots 27 (FIG. 2) on each of the two diametrically oppposed barrier strips. The band is pulled snug enough that it moves to the bottom of each of the slots 27. Also the band is typically of a greater diameter than the keyhole or enlargement 29 at the bottom of the slot so that the band will not tend to slide in the slot or out of the slots. In addition, in the event that the band becomes broken during the wrapping procedure, the fact that it is frictionally engaged in the slots will prevent the whole thing from unravelling.

Once the two barrier strips have been thus secured to the limb, and it is determined that the bands are not so tight as to cause discomfort or impede circulation, then the first half of the cast is applied. This is done by using the cast-forming material in a raw or unset state. Materials for making casts are well known and readily available. As an example, a plaster of Paris gauze (which is basically a gauze impregnated with plaster of Paris) can be wrapped back and forth between the barriers 16 around the sector to the left of the plane 36 of FIG. 7. Once this material has been applied, or during the application of it, it is wetted in accordance with conventional cast-making procedures, and permitted to set. As soon as the full thickness desired has been achieved, and this half of a cast has been set or rigidized, the next step can be commenced. The term "rigidized" is used in order to avoid the implication that the only type of cast-forming material which might be used is the aforementioned plaster of Paris gauze. Other materials might also be used in keeping with present technology and future materials technology developments.

Because of the fact that the plaster of Paris gauze is pushed snugly against both barriers in order to be sure that impressions are received in the edges of the cast by the detents 26 in the barrier, and because the barrier is made of a flexible material such as rubber or plastic, it is possible that excessive pressure may tend to bend some of the portions of the rib between successive rubber band slots 27 out of line with one another. In order to minimize this effect, a reinforcing split tube 17 may be employed as mentioned above to keep the various portions of the rib from being pushed over toward the base flanges.

According to one and the preferred aspect of the method, when the first cast half 13 has rigidized, the rubber band 34 can be snipped at each of the locations where it protrudes (is exposed) at the flange 24 adjacent the rib 21. In this way both of the barriers are released except to the extent that the cast half or shell 13 retains them on the limb 33. Reinforcing tubes 17 are then removed from the ribs and the ribs can be slid out from under the edges 37 of the shell 13. Removal is facilitated by the provision of the notches 39 in the horizontally extending flanges 23 and 24. Thus, in addition to these notches facilitating the formation of the barrier strips around corners such as elbows or wrists when they are first installed on the limb, they provide the added feature of facilitating removal of the barrier strips from shell 13, without disturbing the relationship of the shell with respect to the limb.

After removal of the strips 16, the edges 37 of the shell 13 are coated with a suitable release agent. Petroleum jelly is an example. Then the plaster of Paris gauze is applied to the sector of the limb opposite that to which shell 13 was applied. It is applied in the same way as was described with reference to shell 13. As it is applied, care is taken to be sure that it is adequately pushed into the detent cavities in the edges 37 of shell 13 which were formed by the bulges 26 in rib 21 of the barrier strips 16. Care is also taken that the relationship of shell 13 to limb 33 is not disturbed during this procedure. Then the plaster of Paris gauze is permitted to set.

Figure 10:
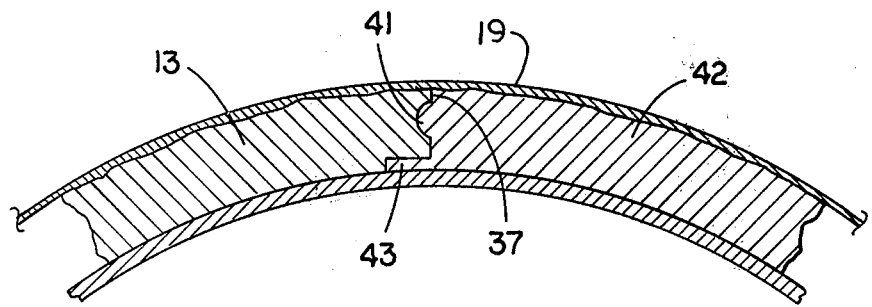
FIG. 10 is a view like FIG. 9 except showing a further step in the method.

When the plaster of Paris gauze has set, it will have thus achieved the appearance shown in FIG. 10 where bulges 41 thereof are provided in each of the cavities of edge 37 of shell 13. Also the new shell 42 is likely to have a flange 43 in the location where the flange 23 of the barrier strip was located during formation of shell 13. The presence of a flange 43 is not essential at all, but it may occur to some extent. In any event, the mating of the bulges 41 with the cavities in the edges of shell 13 prevents any longitudinal movement of shell 42 with respect to shell 13, and also prevents any movement of the one relative to the other in the plane of separation 36. It does accommodate movement of the two shells in the direction 38 perpendicular to the plane of separation or parting line of the shells.

Figure 11:
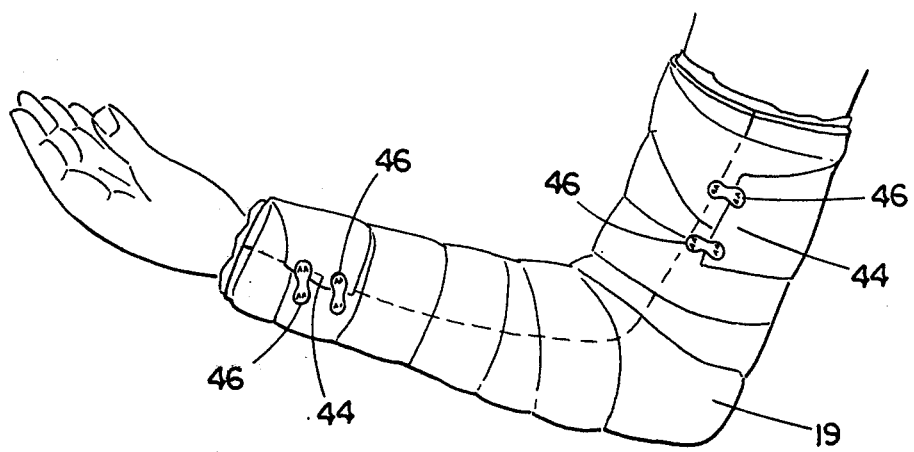
FIG. 11 is a view of a completed arm cast employing an ace bandage binding.

After completion of shell 42, provision is made to thereafter maintain the shells in assembly when the patient leaves the cast room. This is done by providing binder or garter means. One example is shown in FIG. 11 where one or more ace bandage rolls are unwrapped and wound around the pair of shells. The ends 44 of the bandage are secured to the bandage wrapping 19 at the clips 46 in conventional ace bandage wrapping manner.

An alternate way of binding the shells together is the use of strips 47 adhesively or otherwise secured to one or both shells, and which are secured together at their ends 48 by Velcro-type material.

Figure 12:
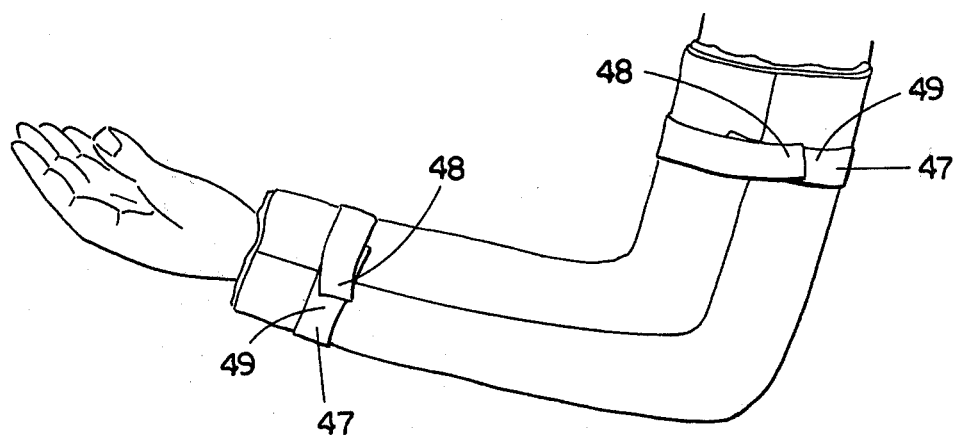
FIG. 12 is a view similar to FIG. 11 with the exception that Velcro-type strips are employed as the binders.

The advantage to having the cast which is removable by separation of two shells has been described above and is described in some of the above-mentioned references. It permits inspection of wounds or incisions, removal of stitches, application of new dressings, and all of this without the necessity of making a new cast each time. Thus it is of significant assistance in better procedures for monitoring patients' progress and minimizing patients' concern over inconvenience and delay of having a cast wholly or partially cut open, removed, and a new cast prepared. An added advantage of the cast according to the present invention is the fact that it accommodates swelling which may result from inflammation or growth. This is achieved by providing suitable resilience in the garter binding of the shells together. It can be accomplished by using an elastic portion in the Velcro-type fastening bands such as at 49 in FIG. 12, for example. It can also be provided by the natural elasticity incorporated in the ace-type bandage. Obviously the number and thickness of turns of the ace bandage can be varied as desired to provide the needed security against separation such as would harm the desired immobilization function, and yet accommodate any anticipated growth or unanticipated swelling due to inflammation. It would also provide easy means for relieving binding and subsequent circulation problems which might be caused as a result of swelling and which could not otherwise be relieved without the attention of a skilled technician who could cut open a conventional cast. Yet it is not encumbered by the extra space and weight which would be attendant the separable casts according to prior art teachings.

While there have been described above the principles of this invention in connection with specific apparatus, it is to be clearly understood that this description is made only by way of example and not as a limitation in the scope of the invention.

What is claimed is:

1. A method of making an immobilizing cast comprising the steps of:
    securing on the body portion to be encased, first and second barriers in circularly spaced relationship;
    applying to a first sector of said body portion between faces of said barriers, a flexible dressing material;
    forming detents in said dressing material at said barriers to provide detented edges on said material;
    rigidizing said dressing material to form a rigid first shell;
    removing said barriers while retaining said first shell in place on said first sector;
    applying to a second sector of said body portion between said edges a flexible dressing material;
    forming at said edges detents in said flexible dressing material on said second sector mating with said detents in said first shell; and
    rigidizing said dressing material to form a rigid second shell.

2. The method of claim 1 and further comprising the step of:
    applying a release agent to the detented edges of said first shell before the step of applying dressing material to the second sector.

3. The method of claim 1 wherein:
    the securing step comprises wrapping an elastic band around said body portion and said barriers and receiving said band in locating slots in said barriers.

4. The method of claim 3 wherein:
    the removing step comprises cutting said band to free said barriers from constraint by said band.

5. The method of claim 1 and further comprising the step of:
    applying garter band means to said shells to retain said shells on said body portion.

6. The method of claim 5 wherein:
    the step of applying said garter band means includes wrapping said shells with elasticized bandage webbing.

7. The method of claim 5 wherein:
    the step of applying said garter band means includes securing "Velcro" type fastening bands across the junctions of mating edges of said shells.

* * * * *